(12) United States Patent
Sulsky et al.

(10) Patent No.: US 6,919,323 B2
(45) Date of Patent: Jul. 19, 2005

(54) PYRIDAZINONE INHIBITORS OF FATTY ACID BINDING PROTEIN AND METHOD

(75) Inventors: Richard Sulsky, West Trenton, NJ (US); Jeffrey A. Robl, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 40 days.

(21) Appl. No.: 10/194,028

(22) Filed: Jul. 12, 2002

(65) Prior Publication Data

US 2003/0040516 A1 Feb. 27, 2003

Related U.S. Application Data

(60) Provisional application No. 60/305,356, filed on Jul. 13, 2001.

(51) Int. Cl.[7] ............... A61K 31/50; A61K 31/675; C07D 237/14; C07D 237/16; C07F 9/6509
(52) U.S. Cl. ............ 514/85; 514/247; 514/252.05; 544/232; 544/238; 544/239; 544/240
(58) Field of Search ................ 544/239, 232, 544/238, 240; 514/247, 85, 252.05

(56) References Cited

U.S. PATENT DOCUMENTS

| | | | |
|---|---|---|---|
| 4,275,069 A | 6/1981 | Youngdale | |
| 5,627,210 A | 5/1997 | Valerio et al. | |
| 6,147,098 A | 11/2000 | Mogensen et al. | |
| 6,403,586 B1 | 6/2002 | Ohkuchi et al. | |

FOREIGN PATENT DOCUMENTS

| | | |
|---|---|---|
| DE | 3627246 | 2/1988 |
| WO | WO 96/38421 | 12/1996 |
| WO | WO 99/32448 | 7/1999 |
| WO | WO 99/44995 | 9/1999 |
| WO | WO 00/15229 | 3/2000 |
| WO | WO 00/15230 | 3/2000 |
| WO | WO 00/59506 | 10/2000 |
| WO | WO 01/54694 | 8/2001 |
| WO | WO 02/40448 | 5/2002 |

OTHER PUBLICATIONS

CAPLUS 105:93875/DN, Chemical Abstracts, Schlimme et al. (1986).
Shibata, K., Agric.Biol.Chem. vol. 53, No. 12, pp. 3355–3356 (1989).
CAPLUS 136:53682/DN, Chemical Abstracts, Nagato et al. (2001).
Gotthardt, H., et al., Chem.Ber. vol. 119, pp. 1315–1330 (1986).

Primary Examiner—Emily Bernhardt
(74) Attorney, Agent, or Firm—Joseph C. Wang

(57) ABSTRACT aP2 inhibiting compounds are provided having the formula

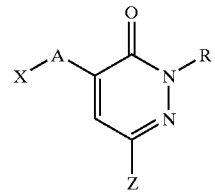

wherein A, X, R and Z are as described herein.

A method is also provided for treating diabetes and related diseases, especially Type II diabetes, employing such aP2 inhibitors alone or in combination with other therapeutic agents, including other antidiabetic agent such as metformin, glyburide, troglitazone and/or insulin.

9 Claims, No Drawings

PYRIDAZINONE INHIBITORS OF FATTY ACID BINDING PROTEIN AND METHOD

This application claims priority to U.S. Provisional Application Ser. No. 60/305,356 filed Jul. 13, 2001, the entirety of which is incorportated herein by reference.

FIELD OF THE INVENTION

The present invention relates to pridazinone inhibitors of fatty acid binding protein (aP2) and to a method for treating diabetes, especially Type II diabetes, as well as hyperglycemia, hyperinsulinemia, obesity, Syndrome X, diabetic complications, atherosclerosis and related diseases, and other chronic inflammatory and autoinimune/inflammatory diseases, employing such pyridazinones alone alone or in combination with one or more types of therapuetic agents.

BACKGROUND OF THE INVENTION

Fatty acid binding proteins (FABPs) are small cytoplasmic proteins that bind to fatty acids such as oleic acids which are important metabolic fuels and cellular regulators. Dysregulation of fatty acid metabolism in adipose tissue is a prominent feature of insulin resistance and the transition from obesity to non-insulin dependent diabetes mellitus (NIDDM or Type II diabetes).

aP2 (adipocyte fatty binding protein), an abundant 14.6 KDa cytosolic protein in adipocytes, and one of a family of homologous intracellular fatty acid binding proteins (FABPs), is involved in the regulation of fatty acid trafficking in adipocytes and mediates fatty acid fluxes in adipose tissue. G. S. Hotamisligil et al, "Uncoupling of Obesity from Insulin Resistance Through a Targeted Mutation in aP2, the Adipocyte Fatty Acid Binding Protein", Science, Vol. 274, Nov. 22, 1996, pp. 1377–1379, report that aP2-deficient mice placed on a high fat diet for several weeks developed dietary obesity, but, unlike control-mice on a similar diet, did not develop insulin resistance or diabetes. Hotamisligil et al conclude "aP2 is central to the pathway that links obesity to insulin resistance" (Abstract, page 1377).

U.S. application Ser. No. 09/391,053, filed Sep. 7, 1992, and U.S. application Ser. No. 09/519,079, filed Mar. 6, 2000, corresponding to U.S. Pat. No. 6,548,529 and U.S. Divisional Application Ser. No. 10/321,137, filed Dec. 17, 2002, disclose a method of treating diabetes employing an aP2 inhibitor.

DESCRIPTION OF THE INVENTION

In accordance with the present invention, pyridazinone compounds are provided which have the structure of formula I

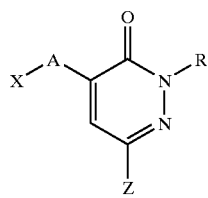

including pharmaceutically acceptable salts thereof, prodrug esters thereof, and all stereoisomers thereof, wherein R is
-J,
—$(CR^3R^4)_n$-J,
—$R^5(CR^3R^4)_p$-J,
—$(CR^3R^4)_m R^5(CR^6R^7)_p$-J,
—$(CR^3R^4)_n(CR^6R^7)_p$-J
—S(O)J where J is other than hydrogen,
—S($O_2$)J where J is other than hydrogen, or
—NH$(CR^3R^4)_n$-J;

J is alkyl, substituted alkyl, cycloalkyl, substituted cycloalkyl, alkenyl, substituted alkenyl, cycloalkenyl, substituted cycloalkenyl, aryl, substituted aryl, heteroaryl, substituted heteroaryl, aralkyl, substituted aralkyl, heteroaralkyl, substituted heteroaralkyl, cycloheteroalkyl or substituted cycloheteroalkyl;

$R^3$ and $R^4$ are the same or different and are independently H, alkyl, cycloalkyl, alkenyl, cycloalkenyl, alkynyl, alkoxycarbonyl, alkylcarbonyl, aminocarbonyl, alkylaminocarbonyl, arylaminocarbonyl, arylcarbonyl, aryl, heteroaryl, halo, hydroxy, alkoxy or aryloxy;
or $R^3$ and $R^4$ together with the atom to which they are bonded may form a 3 to 9-membered saturated or unsaturated ring;

$R^5$ is a bond, O, $NR^8$, S, SO, $SO_2$, CO or CONH;
$R^6$ and $R^7$ are the same or different and are independently H, alkyl, cycloalkyl, aryl, hydroxy, amino, halo, alkoxy, aryloxy, alkylthio, arylthio, alkylamino, dialkylamino, arylamino, diarylamino, alkoxycarbonyl, alkylaminocarbonyl or alkylcarbonylamino;

$R^8$ is H, aryl, arylcarbonyl, alkylaminocarbonyl, arylaminocarbonyl, alkoxycarbonyl, aryloxycarbonyl, alkyl or alkylcarbonyl;

$R^9$ is H, alkyl, substituted alkyl, cycloalkyl, substituted cycloalkyl, cycloheteroalkyl, substituted cycloheteroalkyl, aryl, substituted aryl, aralkyl, substituted aralkyl, heteroaryl, substituted heteroaryl, heteroarylalkyl, substituted heteroarylalkyl or a prodrug ester thereof;

$R^{10}$ is H, alkyl, substituted alkyl, cycloalkyl, substituted cycloalkyl, cycloheteroalkyl, substituted cycloheteroalkyl, aryl, substituted aryl, aralkyl, substituted aralkyl, heteroaryl, substituted heteroaryl, heteroarylalkyl, substituted heteroarylalkyl or a prodrug ester thereof;

$R^{11}$ and $R^{12}$ are the same or different and are independently H, alkyl, substituted alkyl, cycloalkyl, substituted cycloalkyl, cycloheteroalkyl, substituted cycloheteroalkyl, aryl, substituted aryl, aralkyl, substituted aralkyl, heteroaryl, substituted heteroaryl, heteroarylalkyl, substituted heteroarylalkyl or a prodrug ester thereof, A is a bond, methylene, or methylene-oxy (i.e. where -A-X is —$OCH_2$—X);

X is —$CO_2R^9$, —$SO_3H$, —$PO_3R^9R^{10}$, —C(NH)NHOH, —CONHOH, —$CONR^{11}R^{12}$, —$(CR^3R^4)_q$OH, or tetrazole of the formula

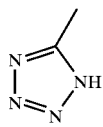

or its tautomer;
n is an integer 0 to 5;
m is an integer 1 to 5;

p is an integer 0 to 4; and q is an integer 1 to 5.

In addition, in accordance with the present invention, a method is provided for treating diabetes, especially Type II diabetes, and related diseases such as insulin resistance, hyperglycemia, hyperinsulinemia, elevated blood levels of fatty acids or glycerol, obesity, hypertriglyceridemia, atherosclerosis, inflammation, diabetic retinopathy, diabetic neuropathy and diabetic neuropathy wherein a therapeutically effective amount of a compound of structure I is administered to a human patient in need of treatment.

In addition, in accordance with the present invention, a method is provided for treating diabetes and related diseases as defined above and hereinafter, wherein a therapeutically effective amount of a combination of a compound of structure I and another type antidiabetic agent is administered to a human patient in need of treatment.

In the above method of the invention, the compound of structure I will be employed in a weight ratio to another antidiabetic agent (depending upon its mode of operation) within the range from about 0.01:1 to about 100:1, preferably from about 0.5:1 to about 10:1.

Examples of X moieties include (but are not limited to)

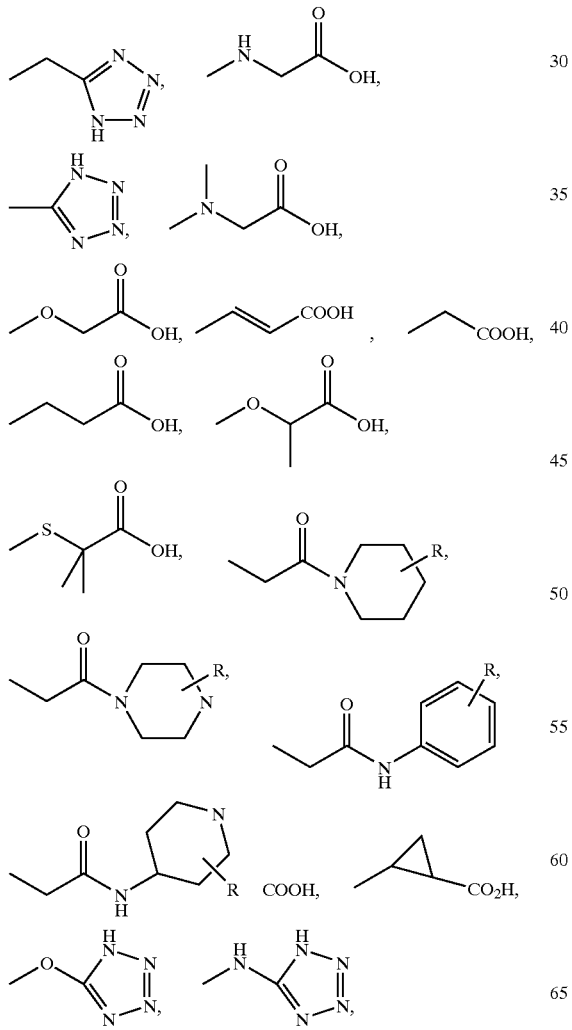

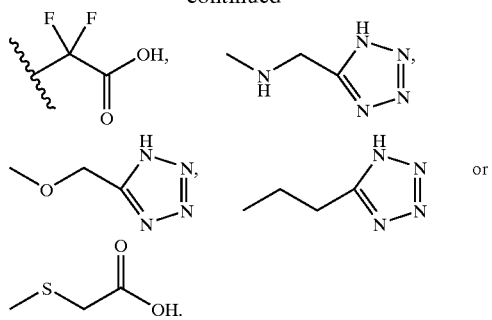

Preferred compounds within the scope of formula I include compounds wherein:

R is —$(CR^3R^4)_n$-J, where n is 1 and $R^3$ and $R^4$ are the same or different and are selected from hydrogen, alkyl and substituted alkyl;

J is optionally substituted aryl (especially substituted with one or more halogen);

A is methylene or methylene-oxy;

X is —$CO_2R^9$, tetrazole, —C(NH)NHOH, —$PO_3R^9R^{10}$, or —CONHOH; and

Z is optionally substituted aryl (especially substituted with one or more alkyl or halogen).

More preferred compounds within the scope of formula I include compounds wherein:

R is —$(CR^3R^4)_n$-J, where n is 1 and $R^3$ and $R^4$ are each hydrogen;

J is optionally substiuted phenyl (especially substituted with one or more halogen, more especially chlorine);

A is methylene;

X is —$CO_2$ $R^9$, or tetrazole; and

Z is optionally substituted phenyl (especially substituted with one or more alkyl or halogen).

DETAILED DESCRIPTION OF THE INVENTION

Compounds of the invention of general structure I may be synthesized as illustrated in the schemes set forth below.

Scheme 1

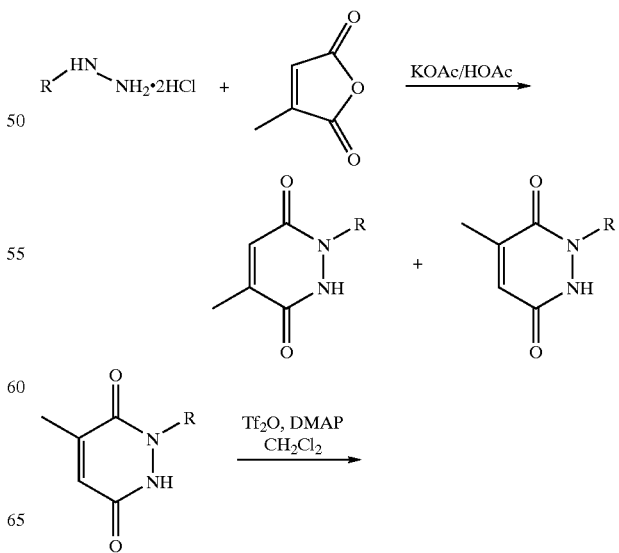

-continued

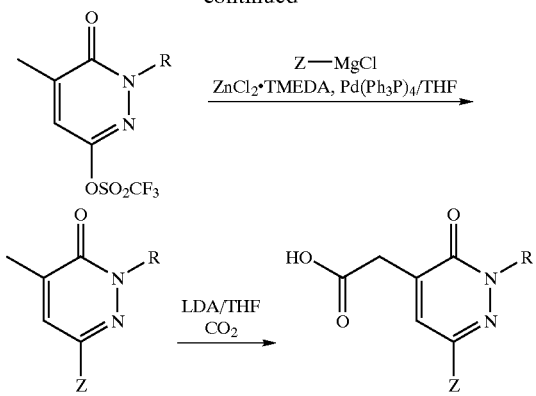

Scheme 2

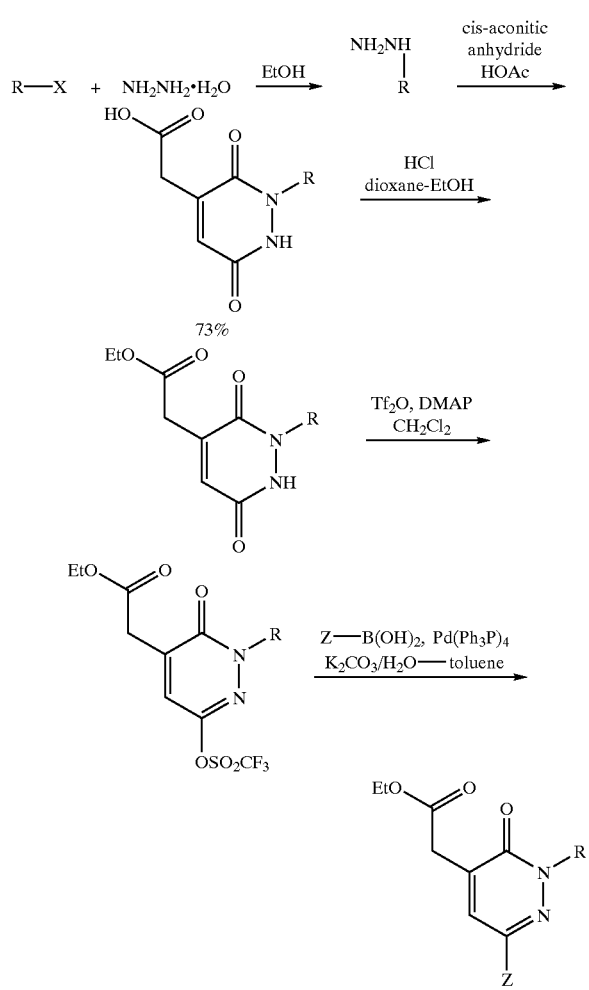

Additional compounds within the scope of formula I can be prepared from the compounds obtained by the above described methods through conversion of the substituent groups to other functionality by the usual methods of chemical synthesis, or may be otherwised sysnthesized using methodology generally known to persons skilled in the art of chemical synthesis.

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkoxy, (alkoxy) alkoxy, alkoxyalkyl, (hydroxy)alkoxyalkyl, (alkoxy) alkoxyalkyl, aryl, aryloxy, (aryl)aryl or diaryl, (aryl) alkoxyaryl, diaryl, arylalkyl, (aryl)alkoxy, (aryl) alkoxyalkyl, (aryloxy)aralkyl, alkenyl, cycloalkyl, cycloalkylalkyl, cycloalkylalkyloxy, amino, substituted amino, alkylamino, hydroxy, hydroxyalkyl, hydroxycarbonyl, alkylcarbonyl, alkoxycarbonyl, arylcarbonyl, acyl, cycloheteroalkyl, (cycloheteroalkyl) alkyl, heteroaryl, heteroaryloxy, heteroarylalkyl, heteroarylalkoxy, aryloxyalkyl, aryloxyaryl, (amino) carbonyl, (substituted amino)carbonyl, alkanoylamino, arylcarbonylamino, nitro, cyano, thiol, haloalkyl, trihaloalkyl and/or alkylthio (where the alkyl radical is optionally substituted), arylthio (where the aryl radical is optionally substituted), sulfonylaryl and/or any of the $R^1$ groups. Where particular substituted alkyl groups are identified herein they are named by adding the term "alkyl" at the end of the name of the substituent radical (e.g., aralkyl, heteroaralkyl etc.).

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, or joined by spiro union to other cycloalkyl rings or heterocycloalkyl rings. Cycloalkyl rings include cyclopropyl, cyclobutyl, cyclopentyl, cyclohexyl, cycloheptyl, cyclooctyl, cyclodecyl and cyclododecyl, cyclohexenyl,

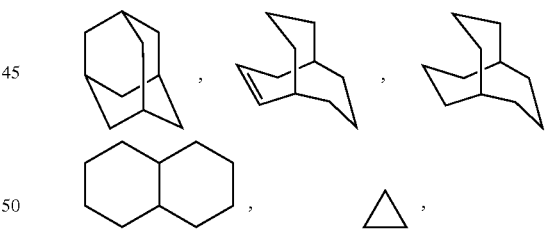

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the $R^1$ groups.

The term "cycloalkenyl" as employed herein alone or as part of another group refers to cyclic hydrocarbons containing 3 to 12 carbons, preferably 5 to 10 carbons and 1 or more double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

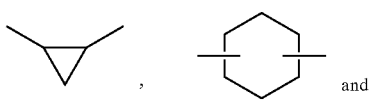

the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio and/or any of the alkyl substituent groups.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

Suitable alkylene, alkenylene or alkynylene groups $(CH_2)_x$ or $(CH_2)_y$ (where, y is 1 to 8, preferably 1 to 5, and x is 1 to 5, preferably 1 to 3, which includes alkylene, alkenylene or alkynylene groups) as defined herein, may optionally include 1, 2, or 3 substituents which include alkyl, alkenyl, halogen, cyano, hydroxy, alkoxy, amino, thioalkyl, keto, $C_3$–$C_6$ cycloalkyl, alkylcarbonylamino or alkylcarbonyloxy.

Examples of $(CH_2)_x$ or $(CH_2)_y$, alkylene, alkenylene and alkynylene include

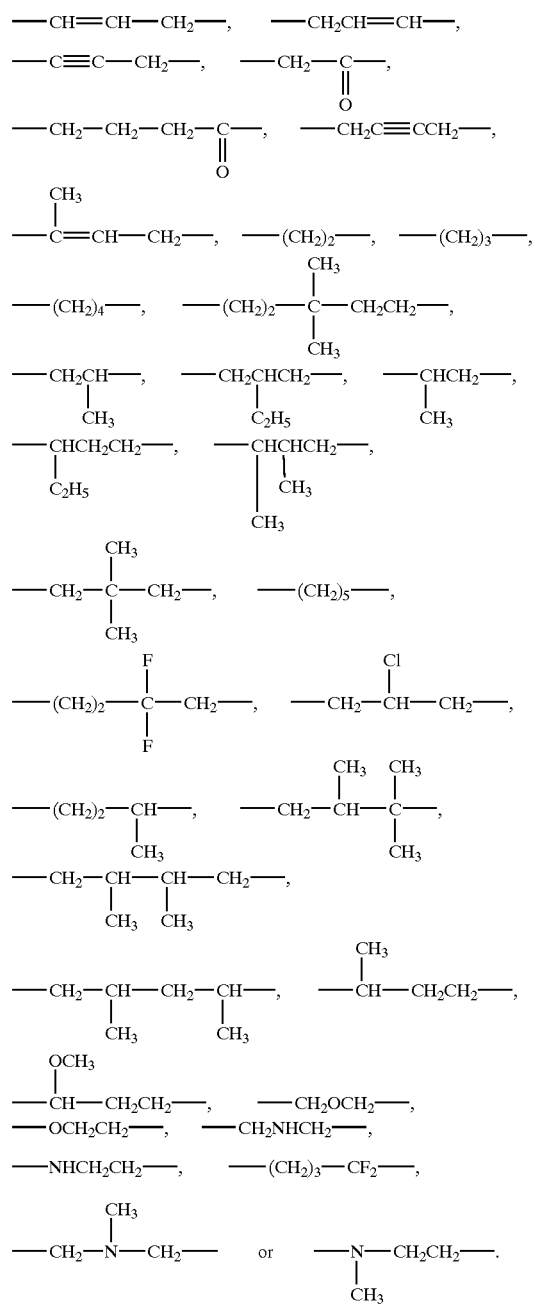

The term "halogen" or "halo" as used herein alone or as part of another group refers to chlorine, bromine, fluorine, and iodine as well as $CF_3$, with chlorine, bromine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the terms "aryl" or "ar" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

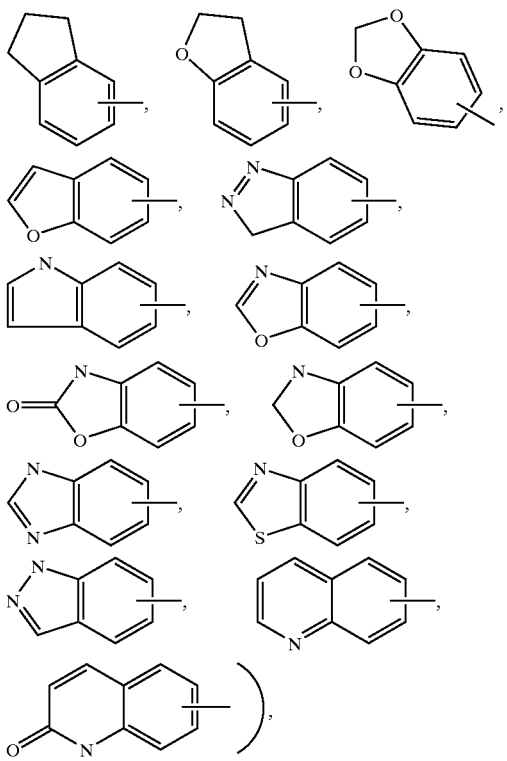

and may be optionally substituted through available carbon atoms with 1, 2, or 3 groups selected from hydrogen, halo, haloalkyl, alkyl, substituted alkyl, alkoxy, haloalkoxy, alkenyl, trifluoromethyl, trifluoromethoxy, alkynyl, cycloalkyl, (cycloalkyl)alkyl, cycloheteroalkyl, cycloheteroalkylalkyl, aryl, substituted aryl, heteroaryl, substituted heteroaryl, (aryl)alkyl, aryloxy, (aryloxy)alkyl, (aryl)alkoxy, arylthio, arylazo, heteroarylalkyl, heteroarylalkenyl, heteroarylheteroaryl, heteroaryloxy, hydroxy, nitro, cyano, amino, substituted amino, thiol, alkylthio, arylthio, heteroarylthio, arylthioalkyl, alkoxyarylthio, alkylcarbonyl, arylcarbonyl, aminocarbonyl, (substituted amino)carbonyl, (alkyl)aminocarbonyl, (substituted alkyl)aminocarbonyl, (aryl)aminocarbonyl, (substituted aryl)aminocarbonyl, alkoxycarbonyl, (amino) alkoxycarbonyl, (substituted amino)alkoxycarbonyl, alkylcarbonyloxy, arylcarbonyloxy, alkylcarbonylamino, arylcarbonylamino, arylsulfinyl, arylsulfinylalkyl, arylsulfonylamino or arylsulfonylaminocarbonyl, sulfonylaryl, (alkyl)sulfonylaryl, sulfonylarylalkyl, (alkyl) sulfonylaralalkyl, and/or any of the R¹ groups.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl (optionally substituted), aryl (optionally substituted), arylalkyl (optionally substituted), arylalkyl (optionally substituted), heteroaryl (optionally substituted), heteroarylalkyl (optionally substituted), cycloheteroalkyl (optionally substituted), (cycloheteroalkyl)alkyl (optionally substituted), cycloalkyl (optionally substituted), cycloalkylalkyl (optionally substituted), haloalkyl (optionally substituted), hydroxyalkyl (optionally substituted), alkoxy-alkyl (optionally substituted) or thioalkyl (optionally substituted). In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, substituted alkyl, alkoxy, alkylthio, halo, trifluoromethyl, hydroxy, aryl or substituted aryl.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl group (i.e.,

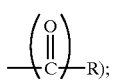

examples of acyl groups include any of the R¹ groups attached to a carbonyl, such as alkanoyl, alkenoyl, aroyl, aralkanoyl, heteroaroyl, cycloalkanoyl, cycloheteroalkanoyl and the like. Such groups may also be identified by adding the term "carbonyl" at the end of the name of the organic radical R bonded to the acyl group (e.g., alkylaminocarbonyl, alkoxycarbonyl, etc).

Unless otherwise indicated, the term "cycloheteroalkyl" as used herein alone or as part of another group refers to a 5-, 6- or 7-membered saturated or partially unsaturated ring which includes 1 or more hetero atoms such as nitrogen, oxygen and/or sulfur, linked through a carbon atom or a heteroatom, where possible, optionally via the linker $(CH_2)_x$, such as

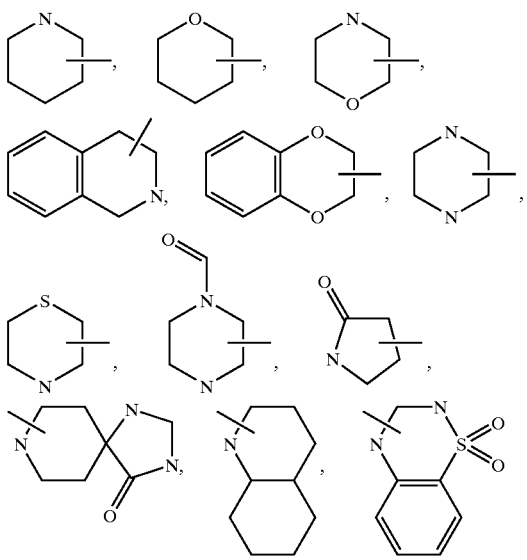

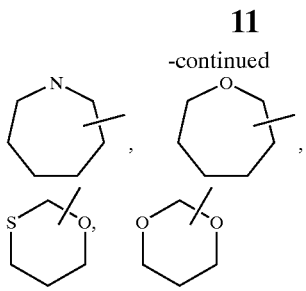

and the like. The above groups may include 1 to 4 substituents such as alkyl, substituted alkyl, halo, oxo, aryl, substituted aryl, aralkyl, substituted aralkyl and/or any of the $R^1$ groups. In addition, any of the cycloheteroalkyl rings can be fused to a cycloalkyl, aryl, heteroaryl or cycloheteroalkyl ring. In addition, any of the cycloheteroalkyl rings can be joined by spiro union to cycloalkyl rings or other heterocycloalkyl rings.

Unless otherwise indicated, the term "heteroaryl" as used herein alone or as part of another group refers to monocyclic and bicyclic aromatic rings containing from 5 to 10 atoms, which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), where the nitrogen and sulfur heteroatoms may optionally be oxidized and the nitrogen heteroatoms may optionally be quaternized. The heteroaryl group may optionally include 1 to 4 substituents such as halo, haloalkyl, alkyl, substituted alkyl, alkoxy, haloalkoxy, alkenyl, trifluoromethyl, trifluoromethoxy, alkynyl, cycloalkyl, cycloalkyl-alkyl, cycloheteroalkyl, cycloheteroalkylalkyl, aryl, substituted aryl, heteroaryl, substituted heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonylaminocarbonyl, sulfonylaryl, sulfonylarylalkyl, and/or any of the $R^1$ groups. Examples of heteroaryl groups include the following:

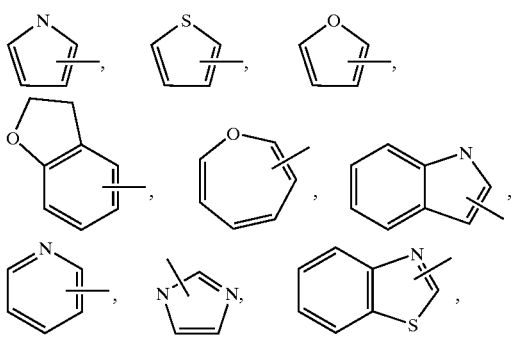

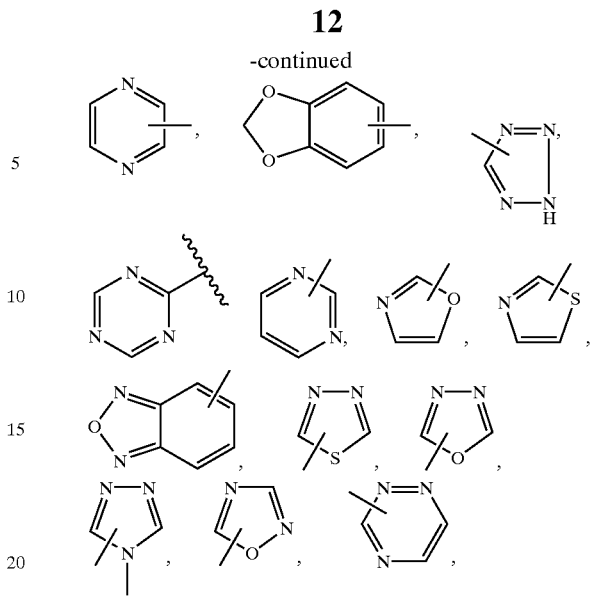

and the like.

The term "cycloheteroalkylalkyl" as used herein alone or as part of another group refers to cycloheteroalkyl groups as defined above linked through a C atom or heteroatom to a $(CH_2)_x$ chain.

The term "heteroarylalkyl" or "heteroarylalkenyl" as used herein alone or as part of another group refers to a heteroaryl group as defined above linked through a C atom or heteroatom to a —$(CH_2)_x$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes prodrug esters which are known in the art for acids such as carboxylic acids including carboxylic acid esters such as methyl, ethyl, benzyl and the like. Other examples of possible prodrug esters include

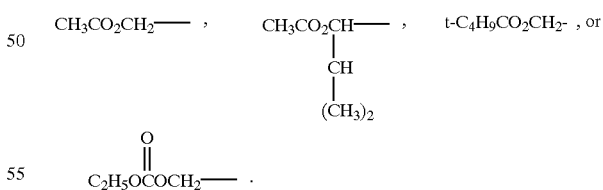

Other examples of suitable prodrug esters include

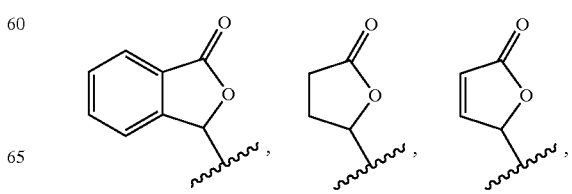

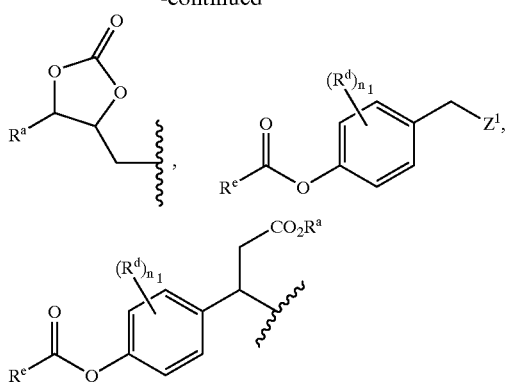

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains a both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

To the extent that compounds of the formula I, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. When diastereomeric or enantiomeric products are prepared, they can be separated by conventional methods for example, chromatographic or fractional crystallization.

Where desired, the compounds of the present invention may be used in combination with one or more hypolipidemic agents or lipid-lowering agents, or lipid agents, or lipid modulating agents, and/or one or more other types of therapeutic agents including antidiabetic agents, anti-obesity agents, antihypertensive agents, platelet aggregation inhibitors, anti-Alzheimer's agents, anti-dementia agents, and/or other cardiovascular agents (including anti-anginal agents, anti-arrhythmic agents, anti-atherosclerosis agents, anti-inflammatory agents, anti-platelet agents, anti-heart failure agents), which may be administered orally in the same dosage form or in a separate oral dosage form, or by injection.

The hypolipidemic agent or lipid-lowering agent or other lipid agent or lipid modulating agent which may be optionally employed in combination with the compounds of the present invention may include 1,2,3 or more MTP inhibitors, HMG CoA reductase inhibitors, squalene synthetase inhibitors, PPAR α agonists, PPAR dual α/γ agonists, PPAR δ agonists, fibric acid derivatives, ACAT inhibitors, lipoxygenase inhibitors, cholesterol absorption inhibitors, ileal $Na^+$/bile acid cotransporter inhibitors, upregulators of LDL receptor activity, cholesteryl ester transfer protein inhibitors, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440. Preferred are each of the preferred MTP inhibitors disclosed in each of the above patents which are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-Trifluoroethoxy)benzoyl]amino]-1-piperidinyl]butyl]-N-(2,2-trifluoroethyl)-9H-fluorene-9-carboxamide

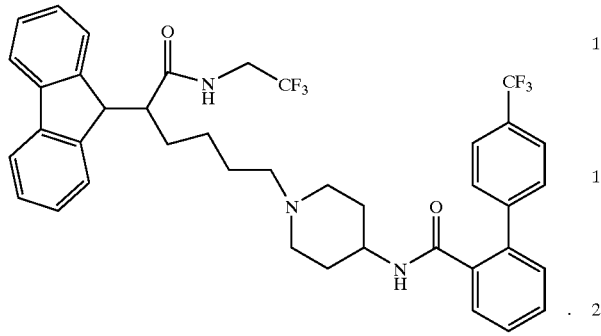

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137 (1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 (ezetimibe) as well as those disclosed in Atherosclerosis 115, 45–63 (1995) and J. Med. Chem. 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425–430 (1999).

The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201;

a beta-lactam cholesterol absorption inhibitor such as disclosed in EP 675714;

an HDL upregulator such as an LXR agonist, a PPAR α-agonist and/or an FXR agonist;

an LDL catabolism promoter such as disclosed in EP 1022272;

a sodium-proton exchange inhibitor such as disclosed in DE 19622222;

an LDL-receptor inducer or a steroidal glycoside such as disclosed in U.S. Pat. No. 5,698,527 and GB 2304106;

an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E;

isoniazid as disclosed in WO 97/35576;

a cholesterol absorption inhibitor, an HMG-CoA synthase inhibitor, or a lanosterol demethylase inhibitor as disclosed in WO 97/48701;

a PPAR δ agonist for treating dyslipidemia;

or a sterol regulating element binding protein-I (SREBP-1) as disclosed in WO 2000/050574, for example, a sphingolipid, such as ceramide, or neutral sphingomyelenase (N-SMase) or fragment thereof.

Preferred hypolipidemic agents are pravastatin, lovastatin, simvastatin, atorvastatin, fluvastatin, pitavastatin and rosuvastatin, as well as niacin and/or cholestagel.

The above-mentioned U.S. patents are incorporated herein by reference. The amounts and dosages employed will be as indicated in the Physician's Desk Reference and/or in the patents set out above or as otherwise known in the art.

The compounds of the present invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent or other lipid agent or lipid modulating agent will be as disclosed in the various patents and applications discussed above.

The dosages and formulations for the other hypolipidemic agent or other lipid agent or lipid modulating agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, or fluvastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The anti-atherosclerotic agent includes a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties," Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of the present invention and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The antidiabetic agent which may be optionally employed in combination with the compounds of the present invention may be 1,2,3 or more antidiabetic agents or antihyperglycemic agents including insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl.

Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms.

The compounds of the present invention will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention will be employed in a weight ratio to the glucosidase inhibitor within the range from about 0.01:1 to about 100:1, preferably from about 0.05:1 to about 10:1.

The compounds of the present invention may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's REZULIN, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention will be employed in a weight ratio to the thiazolidinedione in an amount within the range from about 0.01:1 to about 100:1, preferably from about 0.05:1 to about 10:1.

The sulfonyl urea and PPAR γ agonists in amounts of less than about 150 mg oral antidiabetic agent may be incorporated in a single tablet with the compounds of the present invention.

The compounds of the present invention may also be employed in combination with a antihyperglycemic agent such as insulin or with glucagon-like peptide-1 (GLP-1) or mimetic such as GLP-1(1–36) amide, GLP-1(7–36) amide, GLP-1(7–37) (as disclosed in U.S. Pat. No. 5,614,492 to Habener, the disclosure of which is incorporated herein by reference), as well as AC2993 (Amylen) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the PPAR anti-diabetic agent may be employed in amounts within the range from about 0.01 to about 2000 mg/day which may be administered in single or divided doses one to four times per day.

Where present insulin and other anti-diabetic agents as set out above may be employed in formulations, amounts and dosing as indicated by the Physician's Desk Reference.

Where present GLP-1 peptides or mimetics may be administered in oral buccal formulations, by nasal administration or parenterally as described in U.S. Pat. Nos. 5,346,701 (TheraTech), 5,614,492 and 5,631,224 which are incorporated herein by reference.

The antidiabetic agent or other lipid agent may also be a PPAR modulator such as a PPAR alpha/gamma dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. application Ser. No. 09/664,598, filed Sep. 18, 2000, (attorney file LA29) the disclosure of which is incorporated herein by reference, employing dosages as set out therein, which compounds designated as preferred are preferred for use herein.

The antidiabetic agent may be an SGLT2 inhibitor such as disclosed in U.S. Pat. No. 6,414,126, employing dosages as set out therein. Preferred are the compounds designated as preferred in the above application.

The antidiabetic agent may be a DP4 inhibitor such as disclosed in U.S. Pat. No. 6,395,767, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydro-isoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compounds of the present invention may be repaglinide or STARLIX (Novartis), nateglinide (Novartis) or KAD1229 (PF/Kissei), with repaglinide being preferred.

The antidiabetic compound may be a melanocortin receptor agonist such as a spiropiperidine as disclosed in WO 99/64002.

The compounds of the present invention will be employed in a weight ratio to the meglitinide, PPAR modulator such as a PPAR gamma agonist, PPAR α agonist, PPAR δ agonits or antagonist, PPAR alpha/gamma dual agonist, DP4 inhibitor or SGLT2 inhibitor or other antidiabetic agent within the range from about 0.01:1 to about 100:1, preferably from about 0.05:1 to about 10:1.

The other type of therapeutic agent which may be optionally employed with the compounds of the present invention may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor beta drug, a PTP-1B inhibitor, an anorectic agent, a PPAR modulator including PPAR γ antagonists, PPAR α agonists, PPAR δ antagonists, a CCKA agonist, a leptin inhibitor such as a leptin receptor activator, a neuropeptide Y antagonist, a melanocortin-4-receptor (MC4R) agonist, a fatty acid oxidation upregulator or inducer (such as FAMOXIN Genset).

The beta 3 adrenergic agonist which may be optionally employed in combination with the compounds of the present invention may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750, 355 and CP331648 being preferred.

The neuropeptide Y antagonists which may be optionally employed in combination with the compounds of the present invention include those described in WO 0113917 (BMS) or in U.S. Pat. No. 6,218,408 (Synaptic) and in WO 0114376 (Banyu).

The lipase inhibitor which may be optionally employed in combination with compounds of the present invention may be orlistat or ATL-962 (Alizyme), with orlistat being preferred.

The serotonin (and dopoamine) reuptake inhibitor which may be optionally employed in combination with compounds of the present invention may be sibutramine, topiramate (Johnson & Johnson) or axokine (Regeneron), with sibutramine and topiramate being preferred.

The thyroid receptor beta compound which may be optionally employed in combination with compounds of the present invention may be a thyroid receptor ligand as disclosed in WO097/21993 (U. Cal SF), WO99/00353 (KaroBio), GB98/284425 (KaroBio), and WO 01/60784, with compounds of the KaroBio applications and WO 01/60784 being preferred.

The anorectic agent which may be optionally employed in combination with compounds of the present invention may be dexamphetamine, phentermine, phenylpropanolamine or mazindol, with dexamphetamine being preferred.

The CCKA agonists which may be employed herein include Glaxo-SmithKline's GI-181,771 and Sanofi's SR146,131.

The PTP-1B inhibitor which may be an anti-oesity and/or an antidiabetic agent include those disclosed in WO 99/585, 521, WO 99/58518, WO 99/58522 and WO 99/61435.

The anti-obesity agent employed may also be Pfizer's P57 or CP-644,673.

The various anti-obesity agents described above may be employed in the same dosage form with the compounds of the present invention or in different dosage forms, in dosages and regimens as generally known in the art or in the PDR.

The antihypertensive agents which may be employed in combination with the compounds of the invention include ACE inhibitors, angiotensin II receptor antagonists, NEP-inhibitors such as candoxatril, NEP/ACE inhibitors, as well as calcium channel blockers (such as verapamil and amlodipine besylate), T-channel calcium antagonists (such as mibefradil), β-adrenergic blockers, diuretics, α-adrenergic blockers (such as doxazosin mesylate and terazosin HCl), dual action receptor antagonists (DARA), heart failure drugs such as digoxin, and other types of antihypertensive agents.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-t-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and Curr. Ther. Res. 40:74 (1986); Ru 44570 (Hoechst) disclosed in Arzneimittelforschung 34:1254 (1985), cilazapril (Hoffman-LaRoche) disclosed in J. Cardiovasc. Pharmacol. 9:39 (1987); R 31–2201 (Hoffman-LaRoche) disclosed in FEBS Lett. 165:201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. clin. Pharmacol. 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl)disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, U.S. Pat. No. 5,552,397, U.S. Pat. No. 5,504,080, U.S. Pat. No. 5,612,359, U.S. Pat. No. 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, gemopatrilat ([S [(R*,R*)]-hexahydro-6-[(2-mercapto-1-oxo-3-phenylpropyl)amino]-2,2-dimethyl-7-oxo-1H-azepine-1-acetic acid) and CGS 30440.

The angiotensin II receptor antagonist (also referred to herein as angiotensin II antagonist or AII antagonist) suitable for use herein includes, but is not limited to, irbesartan, losartan, valsartan, candesartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist will be as set out in the latest edition of the Physician's Desk Reference (PDR).

Dual action receptor antagonists (DARA) suitable for use herein include those disclosed in U.S. applications Ser. No. 09/513,779, filed Feb. 25, 2000, and Ser. No. 09/604,322, filed Jun. 26, 2000.

Other examples of preferred antihypertensive agents suitable for use herein include omapatrilat (VANLEV), gemopatrilat, amlodipine besylate (NORVASC), prazosin HCl (MINIPRESS), verapamil, nifedipine, diltiazem, felodipine, nisoldipine, isradipine, nicardipine, beta blockers such as nadolol, atenolol (TENORMIN), sotalol, terazosin, doxazosin, carvedilol, and propranolol, and clonidine HCl (CATAPRES).

Diuretics which may be employed in combination with compounds of the present invention include hydrochlorothiazide, torasemide, furosemide, spironolactone, and indapamide.

Antiplatelet agents which may be employed in combination with compounds of the present invention include aspirin, clopidogrel, ticlopidine, dipyridamole, abciximab, tirofiban, eptifibatide, anagrelide, and ifetroban, with clopidogrel and aspirin being preferred.

The antihypertensive agents, diuretics and antiplatelet drugs may be employed in amounts as indicated in the PDR. Ifetroban may be employed in amounts as set out in U.S. Pat. No. 5,100,889.

Anti-Alzheimer's agents or anti-dementia agents suitable for use herein include tacrine HCl (COGNEX) and donepezil (ARICEPT), as well as γ-secretase inhibitors, β-secretase inhibitors and/or antihypertensive agents. Dosages employed will be as set out in the PDR.

a cyclooxygenase (COX)-2 inhibitor, such as celecoxib, rofecoxib or paracoxib or a glycoprotein IIa/IIIb receptor antagonist such as disclosed in WO 99/45913 and tirofiban or abciximab;

a 5-HT reuptake inhibitor such as disclosed in WO 99/44609;

anti-anginal agents such as vasodilators, for example, isosorbide dinitrate, or nitroglycerin;

anti-atherosclerosis agents such as ACAT inhibitors and lipoxygenase inhibitors as described herein and phospholipase A-2 inhibitors such as S-3013 and SB-435,495 (which are also anti-inflammatory agents); or an immunosuppressant (for use in transplantations) such as cyclosporine, mycophenolate mofetil, azathioprine and the like.

It will be appreciated that unless otherwise specified the dosage regiment for therapeutic agents used in combination with the compounds of the invention will be as specified in the PDR.

In carrying our the method of the invention, a pharmaceutical composition will be employed containing the compounds of structure I, with or without another therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 20 and 2,000 mg per day, which can be administered in a single dose or in the form of individual doses from 1–4 times per day.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

aP2 inhibitor activity of the compounds of the invention may be determined by use of an in vitro assay system which measures the potentiation of inhibition of aP2 by displacement of a fluorescent substrate from aP2 by the inhibitor. Inhibition constants (Ki values) for the aP2 inhibitors of the invention may be determined by the method described below:

Production of purified recombinant human aP2 protein.
  Recombinant human aP2 protein is produced by standard recombinant DNA technology. In the typical case, aP2 is produced by heterologous expression in *E. coli* strain BL21(D53) transformed with pETlla vector containing the full length human aP2 cDNA (Baxa, C. A., Sha, R. S., Buelt, M. K., Smith, A. J., Matarese, V., Chinander, L. L., Boundy, K. L., and Bernlohr, D. A. (1989). Human adipocyte lipid-binding protein: purification of the protein and cloning of its complementary DNA. Biochemistry 28: 8683–8690 and Xu, Z., Buelt, M. K., Banaszak, L. J., and Bemlohr, D. A. (1991). Expression, purification and crystallization of the adipocyte lipid binding protein. J. Biol. Chem. 266:14367–14370). Purification of aP2 from *E. coli* is conducted as described by Xu, yielding essentially homogeneous aP2 protein with molecular weight ~14600 daltons and free of endogenous fatty acids. The purified aP2 is capable of binding up to one mole of free fatty acid per mole protein. The binding and structural properties of recombinant aP2 protein were previously shown to be identical to aP2 protein isolated from adipose tissue.

In vitro assay of aP2 inhibitors. Inhibitors of aP2 are evaluated in a homogeneous fluorescent-based competition assay using recombinant aP2 protein and 1,8-anilino-naphthalene-sulfonic acid (1,8-ANS) as assay substrate. This competition assay was adapted from generalized procedures described previously (Kane, C. D. and Bernlohr, D. A. (1996). A simple assay for intracellular lipid-binding proteins using displacement of 1-anilino-8-sulfonic acid. (1996) Anal. Biochem. 233:197–204 and Kurian E., Kirk, W. R. and Prendergast, F. G. (1996) Affinity of fatty acid for r-rat intestinal fatty acid binding protein. Biochemistry, 35, 3865–3874). The method relies on the increase in fluorescence quantum yield of 1,8-ANS upon binding to the fatty acid binding site of aP2. The assay is run using appropriate concentrations of inhibitor, 1,8-ANS, and aP2 protein, in order to calculate the inhibitor binding constant (Ki) for compounds being evaluated. The Ki calculation was based on the procedure previously described for calculation of dissociation constants described by Kurian. Lower Ki values indicate higher affinities of compounds binding to aP2.

In the assay as conducted for the inhibitors described herein, a series of aliquots of aP2 (5 $\mu$M) in solution in 10 mM potassium phosphate buffer (pH 7.0) are mixed with an equimolar concentration of test compound, followed by the addition of a series of increasing concentrations of 1,8-ANS (from 0 to 5 $\mu$M). The assay typically is conducted in 96-well plate format with reagents added using robotic instrumentation (Packard Multiprobe 104). The fluorescence value for each test is determined using a Cytofluor-4000 multi-well fluorescence plate reader (Perceptive Biosystems) using excitation wavelength 360 nm and emission wavelength 460 nm, or using other suitable spectrofluorometer. In preparation for the assay, test compounds are initially prepared at 10 mM in dimethylsulfoxide. All subsequent dilutions and assay additions are made in 10 mM potassium phosphate buffer, pH 7.0.

X-ray crystallography of the inhibitor-aP2 complex can be performed by one skilled in the art using contemporary biophysical methodologies and commercial instrumentation. Such crystallographic data can be used to conclusively determine if a compound used in the present invention has embodied the structural requirement necessary for inhibition of aP2. An example of such an X-ray crystallographic determination is presented below:

Crystals of aP2 complexed with the inhibitors were typically grown by the hanging drop method. aP2, at 8.3 mg/ml, was pre-equilibrated with 1–5 mM of the inhibitor in 0.1 M Tris-HCl pH 8.0, 1% w/v DMSO for four hours. 2 $\mu$l drops containing equilibrated protein and reservoir solution at a 1:1 ratio were suspended on plastic cover slips and equilibrated against a 1 ml reservoir containing 2.6–3.0 M ammonium sulfate in 0.1 M Tris-HCl pH 8.0. Crystals typically appeared in 2–3 days and reached maximum size within 2 weeks. Data was typically collected on a single flash-frozen crystal (Oxford Cryosystems) using a Rigaku rotating anode and an R-axis II image plate detector of a Bruker multiwire area detector. Diffraction from aP2 crystals was excellent. Diffraction was consistently observed to better than 2.0 Å resolution often to beyond 1.5 Å resolution. Data was processed either with DENZO/SCALEPACK (R-axis II data), or Xengen (Bruker data). XPLOR was used for structure refinement and model building was done using the molecular modeling package CHAIN. After a single round of refinement, examination of the $F_o$–$F_c$ map typically allowed facile building of the inhibitor into aP2 binding cavity. Iterative fitting and refinement were continued until improvement was no longer seen in the electron density map or R-free.

The following Examples illustrate embodiments of the present invention, and are not intended to limit the scope of the claims. Abbreviations employed herein are defined below. Compounds of the Examples are identified by the example and step in which they are prepared (for example, "1A" denotes the title compounds of step A of Example 1), or by the example only where the compound is the title compound of the example (for example "4" denotes the title comound of Example 4).

9-BBN=9-borabicyclo[3.3.1]nonane
Calc=calculated
DiBAl=diisobutylaluminum hydride
DMAP=Dimethylaminopyridine
DMF=dimethylformamide
DMSO=dimethylsulfoxide
Et=ethyl
Fnd=found
h=hours
LC/MS=liquid chromatography/mass spectrometry
LDA=lithium diisopropylamide
Me=methyl
Ms=mesyl=methanesulfonyl
OAc=acetate
Ph=phenyl
TFA=trifluoroacetic acid
THF=tetrahydrofuran
TMS=trimethylsilyl

EXAMPLE 1

A slurry of citraconic anhydride (5.61 g, 50.0 mmol), benzylhydrazine dihydrochloride (9.80 g, 50.0 mmol) and potassium acetate (9.80 g, 100 mmol) in acetic acid (100 mL) was heated to reflux for 17 h. The reaction mixture was cooled and filtered. The filtrate was evaporated under reduced pressure and re-evaporated from toluene. The gummy yellow residue was partitioned between sodium carbonate solution (90 mL, 4 N) and EtOAc (50 mL). The aqueous extract was washed once with EtOAc and then slowly added to hydrochloric acid (3 M, 140 mL). The resulting white precipitate was collected, washed with water and dissolved in chloroform (1 L). The insoluble material was collected and boiled in EtOAc and filtered hot, to give 1,2-dihydro-1-benzyl-4-methyl-3,6-pyridazinedione as a white solid, mp >200° C. (1.85 g, 17%). Part IA compound.

The organic extracts from Part IA were combined, dried (MgSO$_4$) and evaporated onto silica gel (30 g). Purification by flash chromatography on silica gel (5×25 cm column, 1:3 EtOAc/hexanes) gave Part IB compound, 1,2-dihydro-1- benzyl-5-methyl-3,6-pyridazinedione as a white solid, mp >200° C. (2.35 g, 22%).

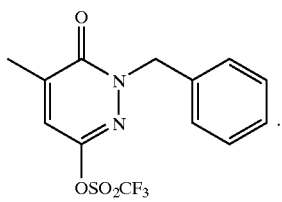

II

To a stirred solution of part IB compound (1.785 g, 8.25 mmol) and DMAP (2.01 g, 16.5 mmol) in $CH_2Cl_2$ (20 mL) at −25° C. under argon was added triflic anhydride (1.43 mL, 8.30 mmol), dropwise, over 5 min. After 15 min, the reaction mixture was diluted with $CH_2Cl_2$ and washed once with hydrochloric acid (1 M, 20 mL). The organic layer was dried ($MgSO_4$) and evaporated. Purification by flash chromatography (5×10 cm column, $CH_2Cl_2$) gave Part II compound as a colorless oil (2.85 g, 99%).

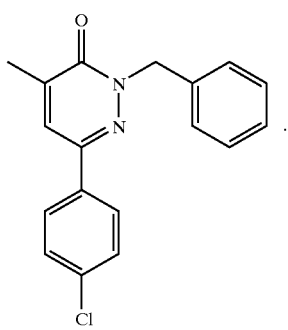

III

A stirred solution of 4-chlorophenylmagnesium chloride (5.0 mL, 5.0 mmol, 1 M in $Et_2O$) was evaporated to dryness and redissolved at room temperature under Ar in THF (10 mL). The solution was treated $ZnCl_2$TMEDA complex (1.26 g, 5.0 mmol) and stirred for 20 min. To this solution was added a $N_2$-purged Part II compound (818 mg, 2.35 mmol) in THF (10 mL) and palladium (0) tetrakistriphenylphosphine (200 mg, 0.2 mmol). The mixture was heated to reflux as the solution turns from yellow to black. After 2 h, the reaction was cooled, diluted with EtOAc and washed once with saturated $NaHCO_3$ solution. The organic extract was dried ($MgSO_4$) and evaporated. Purification by flash chromatography (1:4 EtOAc/hexane) gave the title compound as a light yellow amorphous solid, 720 mg, 99% yield.

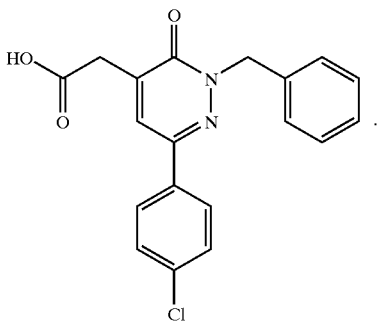

IV

To a stirred solution of LDA (10 mmol, 1.72 M in 6:1 THF/hexanes) at −72° C. under argon was added a solution of part m compound (565 mg, 1.82 mmol) in THF (3 mL) over 20 min. After an additional 15 min, the deep red-purple solution was treated with a stream of dry carbon dioxide gas as the temperature was allowed to rise to −20° C. over 90 min. The resulting yellow solution was quenched with hydrochloric acid (1 M) and extracted three times with EtOAc. The organic extracts were combined, dried ($MgSO_4$) and evaporated. Trituration of the residue gave the title compound as a white solid (186 mg, 29%), mp 200–202° C.

EXAMPLE 2

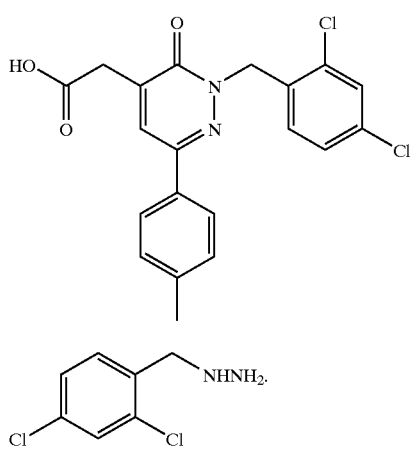

I

To a refluxing solution of hydrazine hydrate (12.2 mL, 250 mmol) in ethanol (50 mL) under argon was added a solution of α,2,4-trichlorotoluene (9.77 g, 50.0 mmol) in ethanol (10 mL) over 30 min. The solution was refluxed for 3 h and then cooled. At atmospheric pressure the reaction mixture was distilled until the pot temperature reached 90° C. and then cooled again. Distillation was continued at 2 mm Hg until the pot temperature reached 60° C. The residue was dissolved in choroform (100 mL) and washed once with saturated $NaHCO_3$ solution (25 mL). The organic extract was dried ($MgSO_4$) and evaporated at ~20 mm Hg. Distillation of the residue (98–103° C., 95–160µ) gave Part I compound as a water-white liquid (6.95 g, 73%).

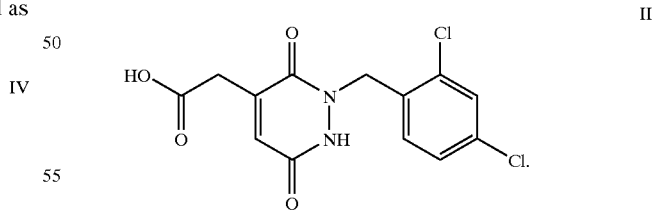

II

To a stirred solution of Part I compound (6.50 g, 34.0 mmol) in HOAc (25 mL) at room temperature under argon was added cis-aconitic anhydride (5.30 g, 34.0 mmol). An exothermic reaction takes place as a thick precipitate formed. The mixture was refluxed for 20 h, cooled, filtered and the collected solid washed with EtOAc. Air drying gave Part II compound as a white solid, mp >200° C. (6.20 g, 55%).

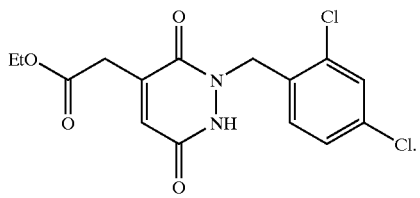

III

A stirred slurry of Part II compound (6.00 g, 18.2 mmol) in EtOH (100 mL) and hydrogen chloride (12 mL, 4 N in dioxane, 48 mmol) was heated to reflux for 1 h. The resulting colorless solution was cooled and evaporated to give Part III compound as a white solid (6.30 g, 97%).

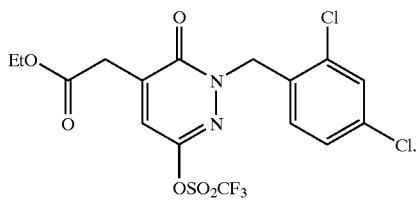

IV

To a stirred solution of part III compound (5.903 g, 16.53 mmol) and DMAP (4.05 g, 31.1 mmol) in $CH_2Cl_2$ (50 mL) at −20° C. under argon was added triflic anhydride (2.83 mL, 16.5 mmol), dropwise, over 5 min. After 15 min, the reaction mixture was diluted with $CH_2Cl_2$ and washed once with hydrochloric acid (1 M, 50 mL). The organic layer was dried ($MgSO_4$) and evaporated. Purification by flash chromatography (5×10 cm column, 1:49 $Et_2O/CH_2Cl_2$) gave Part IV compound as a colorless oil (4.62 g, 99%).

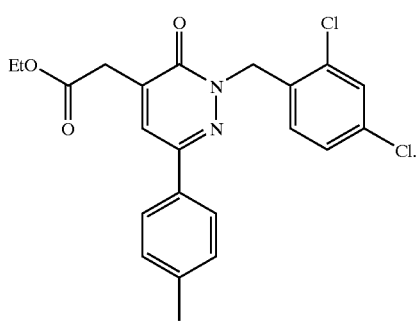

V

To a stirred solution of part IV compound (152 mg, 0.31 mmol) in toluene (2 mL) at room temperature under argon was added 4-tolylboronic acid (63 mg, 0.47 mmol) and sodium carbonate solution (0.35 mL, 0.7 mmol, 2 M in water) and then palladium (0) tetrakistriphenylphosphine (20 mg, 0.017 mmol). The mixture is purged with an argon stream for 15 min and then heated to 50° C. for 30 min. The reaction was cooled to room temperature, quenched with saturated ammonium chloride solution and extracted twice with $CH_2Cl_2$. The extracts were dried ($MgSO_4$) and evaporated. Purification by flash chromatography (2.5×25 cm column, 1:19 $Et_2O/CH_2Cl_2$) gave Part V compound as a light yellow oil (129 mg, 96%).

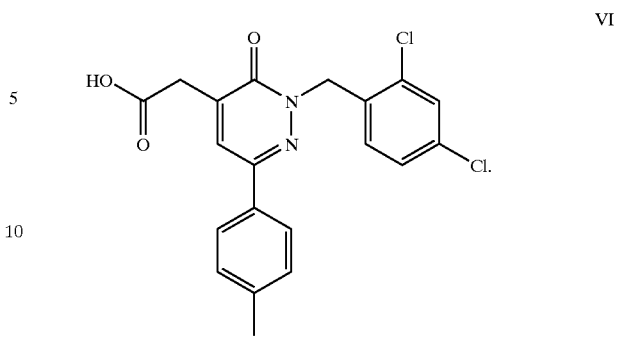

VI

To a solution of Part V compound (125 mg, 0.29 mmol) in dioxane (2 mL) at room temperature under argon, was added a solution of lithium hydroxide monohydrate (42 mg, 1.0 mmol) in water (1 mL). After 1 h, the reaction mixture was acidified to pH 2 with 5% potassium hydrogen sulfate solution and extracted twice with EtOAc. The organic extracts were combined, dried ($MgSO_4$) and evaporated. Recrystallization from $CH_2Cl_2$/hexanes gave the title compound as a white solid, mp 134–136° C. (105 mg, 90%).

EXAMPLE 3

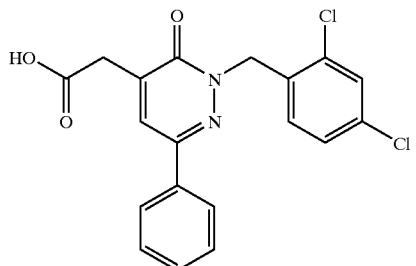

I

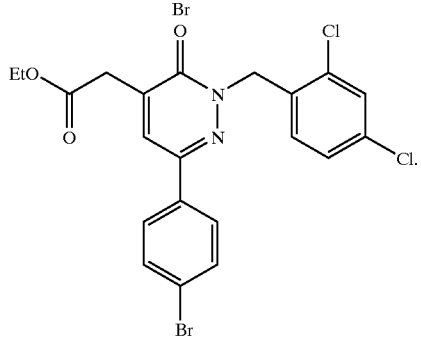

To a stirred solution of Example 2 Part IV compound (485 mg, 1.00 mmol) in toluene (5 mL) at room temperature under argon was added 4-bromoboronic acid (220 mg, 1.1 mmol) and sodium carbonate solution (1.12 mL, 2.2 mmol, 2 M in water) and then palladium (0) tetrakistriphenylphosphine (60 mg, 0.05 mmol). The mixture is purged with an argon stream for 15 min and then heated to 50° C. for 30 min. The reaction was cooled to room temperature, quenched with saturated ammonium chloride solution and extracted twice with $CH_2Cl_2$. The extracts were dried ($MgSO_4$) and evaporated. Purification by flash chromatography (5×15 cm column, 1:49 $EtOAc/CH_2Cl_2$) gave Part I compound as a light yellow oil (280 mg, 56%).

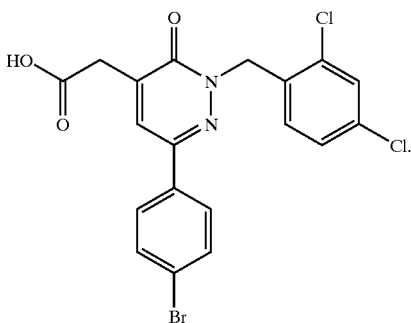

To a solution of Part I compound (275 mg, 0.55 mmol) in dioxane (2 mL) at room temperature under argon, was added a solution of lithium hydroxide monohydrate (80 mg, 1.9 mmol) in water (2 mL). After 1 h, the reaction mixture was acidified to pH 2 with 5% potassium hydrogen sulfate solution and extracted twice with EtOAc. The organic extracts were combined, dried (MgSO$_4$) and evaporated. Recrystallization from CH$_2$Cl$_2$/hexanes gave the title compound as a white solid, mp 144–146° C. (231 mg, 90%).

We claim:

1. A compound of formula I

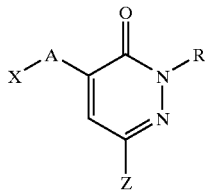

enantiomers, diastereomers, pharmaceutically acceptable salts thereof, prodrug esters thereof wherein R is —(CR$^3$R$^4$)$_n$-J, where n is 1 and R$^3$ and R$^4$ are the same or different and are selected from hydrogen, alkyl or substituted alkyl;

J is an aryl group having 6–10 carbon atoms optionally independently substituted with one or more halogen;

A is methylene or methylene-oxy;

X is —CO$_2$R$^9$, tetrazole, —C(NH)NHOH, —PO$_3$R$^9$R$^{10}$, or —CONHOH; and

Z is an aryl group having 6–10 carbon atoms optionally independently substituted with one or more alkyl and or halogen;

R$^9$ is H or alkyl; and

R$^{10}$ is H or alkyl.

2. A compound of claim 1 wherein

R is —(CR$^3$R$^4$)$_n$-J, where n is 1 and R$^3$ and R$^4$ are each hydrogen;

J is optionally substituted phenyl;

A is methylene;

X is —CO$_2$R$^9$, or tetrazole; and

Z is optionally substituted phenyl.

3. The compound of claim 2 wherein J is phenyl independently substituted with one or more halogen.

4. The compound of claim 2 wherein Z is phenyl independently substituted with one or more alkyl or halogen.

5. The compound of claim 2 wherein X is —CO$_2$R$^9$.

6. The compound of claim 5 wherein R$^9$ is hydrogen or alkyl.

7. A pharmaceutical composition comprising at least one compound of claim 1 together with a pharmaceutically acceptable vehicle or carrier therefor.

8. A method for treating diabetes, insulin resistance, hyperglycemia, hyperinsulinemia, or elevated blood levels of free fatty acids or glycerol, obesity, hypertriglyceridemia, inflammation, atherosclerosis, diabetic retinopathy, diabetic neuropathy or diabetic nephropathy which comprises administering to a mammalian species in need thereof an effective amount of a compound of claim 1.

9. A method for treating diabetes, insulin resistance, hyperglycemia, hyperinsulinemia, or elevated blood levels of free fatty acids or glycerol, obesity, hypertriglyceridemia, inflammation, atherosclerosis, diabetic retinopathy, diabetic neuropathy or diabetic nephropathy which comprises administering to a mammalian species in need thereof an effective amount of a compound of claim 2.

* * * * *